United States Patent [19]
Tracey

[11] Patent Number: 5,246,366
[45] Date of Patent: Sep. 21, 1993

[54] ORTHODONTIC SPRING RETRACTOR

[76] Inventor: Stephen G. Tracey, 22760 Cardinal St., Grand Terrace, Calif. 92324

[21] Appl. No.: 797,306

[22] Filed: Nov. 25, 1991

[51] Int. Cl.$^5$ .................................................. A61C 3/00
[52] U.S. Cl. .................................................. 433/21
[58] Field of Search .................. 433/6, 7, 18, 20, 21

[56] References Cited

U.S. PATENT DOCUMENTS

| | | | |
|---|---|---|---|
| 3,454,001 | 6/1966 | Stockfisch | 433/6 |
| 3,964,165 | 6/1976 | Stahl | 433/21 |
| 4,197,643 | 4/1980 | Burstone et al. | 433/20 |
| 4,255,139 | 3/1981 | Ladanyi | 433/21 |
| 4,580,976 | 4/1986 | O'Meara | 433/21 |
| 4,818,226 | 4/1989 | Berendt et al. | 433/20 |
| 4,975,052 | 12/1990 | Spencer et al. | 433/21 |

OTHER PUBLICATIONS

"The Segmented Arch Approach to Space Closure" article, by C. J. Burstone, *American Journal of Orthodontics*, pp. 361–378, Nov., 1982.
"Auxiliary Springs in Continuous Arch Treatment" article, by Haskell et al., *Am. J. Orthod. Dentofac.*, pp. 488–498, Dec. 1990.
BioTrac ® brochure; RMO Inc., Denver, CO; 4 pp., 1991.

*Primary Examiner*—Robert P. Swiatek
*Assistant Examiner*—Cindy A. Cherichetti
*Attorney, Agent, or Firm*—Sheldon & Mak

[57] ABSTRACT

Disclosed is an orthodontic retraction system that couples to vertical bracket slots, and that is compatible with continuous arches. In one aspect of the invention, a retraction spring that is formed of a high-strength elongate member of uniform cross-section has a stem at one end of the spring for engaging the vertical slot of a first tooth bracket, the stem being bendable for anchoring to the first tooth bracket; a shank extending from the other end of the spring for engaging a horizontally oriented auxiliary passage in a second tooth bracket, the shank also being bendable for anchoring to the second tooth bracket; and a T-shaped loop formed between the stem and the shank for biasingly connecting the tooth brackets. The disclosed system includes the spring and includes a plurality of the tooth brackets for rigid connection to corresponding teeth of a patient, each of the brackets having associated means for anchoring the continuous arch wire. The system is used by feeding the shank of the spring through the auxiliary passage, feeding the stem from the gingival through the vertical slot while applying sufficient moment for aligning the stem vertical, bending a protruding portion of the stem for locking the stem to the first bracket, and bending a protruding portion of the shank while holding the shank in an extending, tensioned condition, the spring transmitting a relatively large restoring moment along with tension forces for avoiding undesired tipping of the retracting teeth.

22 Claims, 1 Drawing Sheet

ORTHODONTIC SPRING RETRACTOR

BACKGROUND

The present invention relates to orthodontics, and more particularly to retraction systems using so-called "edgewise brackets" having vertical slots for auxiliary devices.

A well-known problem in orthodontics is that space closure is hampered by friction between the brackets and the arch wire, especially when tipping occurs. One solution to this problem is the use of segmented arch wires. Retraction springs such as vertical loops are typically used, the springs transmitting retraction forces and moments between the segments. The transmission of moments as well as the forces allows the effective force line of action to be displaced in the gingival direction from the location of the springs for avoiding tipping during retraction. However, segmented arch wires give rise to other difficulties related to first-order alignment, many practitioners preferring continuous arches as a fail-safe approach.

With reference to FIGS. 1a and 2a, a recent development in orthodontics is the use of traditional edgewise tooth brackets 10 having horizontal rectangular archwire slots 11 for receiving an arch wire 12, each bracket 10 further incorporating a rectangular vertical slot 13 that extends between the archwire slot 11 and a base portion of the bracket 10. A variety of auxiliary devices can be engaged with the vertical slot. 13 while the arch wire 12 is in place. As shown in FIG. 1a for example, a "power pin" 14 has a rectangular shank for engaging the vertical slot 13, and a low-profile T-shaped head portion 15 for engaging an elastic or elastomeric tensioner 16. The shank is inserted axially into the slot from the gingival direction, the head portion 15 resting against the bracket 10. The protruding free end of the shank is then bent in the anterior or posterior direction (away from the direction of the tensioner) as indicated at 17 for locking the power pin 14 to the bracket 10, after which the end of the shank is trimmed approximately flush with the bracket 10. A "power hook" (not shown) is formed of square or rectangular wire, having a shank portion at one end of a Z-shaped main portion, the other end of the main portion having a side-facing open hook formed therein for engaging a tensioner. Rotating springs, uprighting springs, and torquing auxiliaries are also conventionally used, a torquing auxiliary spring 18 being shown in FIG. 2a, a main portion being curved in correspondence with the arch wire 12, one end of the spring 18 being formed at right angles and engaging the vertical slot 13 of a bracket 10 as indicated at 19. These auxiliary devices can be applied for correcting individual tooth malpositions whenever needed, because the vertical slots are always available.

Elastomeric auxiliaries are also used for retraction, but these are subject to plastic deformation, the delivered force being severely attenuated shortly after placement. Elastomeric auxiliaries are unable to transmit bending moments. This characteristic is a disadvantage in that there is no way to use the elastomeric to transmit a compensating moment against tipping movements. This produces significantly increased friction between the arch and the brackets, even when uprighting springs are used.

The conventional uprighting springs that are available for engaging the vertical bracket slot also have the disadvantage of that they are coupled directly to the arch wire, with consequent frictional loading between the arch wire and one or more of the brackets.

Thus there is a need for a system for orthodontic retraction that is not subject to the above disadvantages.

SUMMARY

The present invention meets this need by providing an orthodontic retraction spring. In one aspect of the invention, the spring includes a high-strength elongate member of uniform cross-section having a stem portion at a first end of the spring for engaging a vertically oriented slot in a first tooth bracket, the stem portion being bendable for anchoring to the first tooth bracket; a shank portion extending from a second end of the spring for engaging an auxiliary passage in a second tooth bracket, the auxiliary passage being oriented in parallel-spaced relation to a main arch passage of the second tooth bracket, the shank portion being bendable for anchoring to the second tooth bracket; and a loop portion connected between the stem portion and the shank portion for biasingly connecting the tooth brackets, the spring having a tensile spring constant of less than approximately 50 grams per millimeter and being capable of coupling a bending moment to the generic bracket, the bending moment being greater than approximately 500 gram-millimeters. The elongate member can be of uniform rectangular cross-section.

The loop portion can form a T-shaped side profile outline having an upper segment; a pair of semicircular segments joining opposite ends of the upper segment; a pair of arm segments joining respective ones of the semicircular segments opposite the upper segment, the arm segments being aligned approximately parallel to the upper segment; a pair of upper quarter-circular segments joining respective ones of the arm segments opposite the corresponding semicircular segments; first and second parallel-spaced column segments joining respective ones of the upper quarter-circular segments opposite the corresponding arm segments, the column segments being oriented approximately perpendicular to the upper segment; and a lower quarter-circular segment joining the second stem segment opposite the corresponding upper quarter-circular segment, the lower quarter-circular segment joining the shank portion.

The spring can further include a Z-shaped leg portion connected between the loop portion and the stem portion, the leg portion having a leg segment, a first curved segment connecting a first end of the leg segment to the stem portion, and a second curved segment connecting the other end of the leg segment to the first column segment of the loop portion. The leg segment can be inclined upwardly by an angle A from the second leg segment to the first leg segment relative to the shank portion, and the stem portion forms an included angle B with the leg segment, the angle B being greater than 90 degrees.

The elongate member can be formed from a high-strength alloy selected from the group consisting of beta-titanium, a nickel-titanium alloy, and an alloy of cobalt. The spring so formed preferably has a uniform square cross-section of 0.017 inch by 0.017 inch for torsionally engaging the vertically oriented slot. Alternatively, the elongate member can be formed from corrosion resistant steel. The spring so formed preferably has a uniform square cross section of 0.016 inch by 0.016 for obtaining a suitably low tensile spring constant while torsionally engaging the vertically oriented slot.

In another aspect of the invention, an orthodontic retraction apparatus includes a plurality of the tooth brackets for rigid connection to corresponding teeth of a patient, each of the brackets having means for engaging a continuous arch wire, the tooth brackets including a first tooth bracket having a main arch slot and means for anchoring an arch wire tie, and an auxiliary slot for receiving an elongate member, the auxiliary slot being oriented in perpendicular relation to the main arch slot, and a second tooth bracket having a main arch wire passage for receiving the arch wire and an auxiliary passage therethrough, the auxiliary passage being oriented in parallel-spaced relation to the main arch passage; and the retraction spring including the high-strength elongate member having the stem portion, the shank portion, and the loop portion.

The present invention also provides a method for retracting a patient's teeth including the steps of: providing first and second tooth brackets anchored to respective teeth of the patient for engaging a continuous arch wire, the first bracket having a vertically oriented auxiliary slot, the second bracket having a horizontally oriented auxiliary passage; providing the retraction spring including the high-strength elongate member having the stem portion, the shank portion, and the loop portion; feeding the shank of the spring through the auxiliary passage; feeding the stem from the gingival through the vertical slot while applying sufficient moment for aligning the stem vertical; bending a protruding portion of the stem for locking the stem to the first bracket; and bending a protruding portion of the shank while holding the shank in an extending, tensioned condition, the spring transmitting a relatively large restoring moment along with tension forces for avoiding undesired tipping of the retracting teeth.

DRAWINGS

These and other features, aspects, and advantages of the present invention will become better understood with reference to the following description, appended claims, and accompanying drawings, where:

DESCRIPTION

Figure 1A:
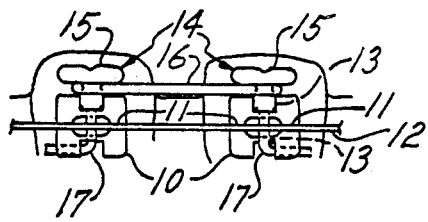
FIG. 1a is a side elevational view of an installed prior art retractor in which an arch wire slidably engages a pair of tooth brackets, and an elastomer is coupled between a pair of power pins that engage vertical slots of the respective brackets.
Figure 2A:
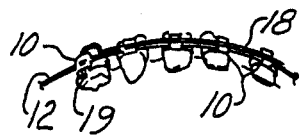
FIG. 2a is a bottom front oblique perspective view showing an installed prior art torquing auxiliary spring, one end of the auxiliary engaging a vertical bracket slot.

The present invention is directed to an orthodontic retraction system that is compatible with continuous arches. With reference to FIGS. 1-5 of the drawings, an orthodontic retraction spring 20 according to the present invention is formed from a suitable length of spring wire of uniform cross-section, the cross-section being preferably rectangular, having a thickness t and a depth d, for efficient utilization of the wire material. The spring 20 has a stem portion 22 at a first spring end 24 for engaging a vertically oriented slot 26 in a first tooth bracket 28, the stem portion 22 being bendable for anchoring to the first tooth bracket 28 as indicated at 30 in FIG. 5. An arch member 32 also engages a counterpart of the archwire slot 11, designated main arch slot 34, of the first tooth bracket 28, as described above in connection with the prior art. A shank portion 36 extends from a second spring end 38 of the spring 20 for engaging an auxiliary passage 40 that is formed in a second tooth bracket 42, the second tooth bracket 42 having a counterpart of the arch slot 34, designated main arch passage 34', that locates the arch member 32. Typically, the second tooth bracket 42 is configured as a "molar bracket" which may be banded, the main arch passage 34' being formed as a tubular portion of the bracket 42. It will be understood that the present invention contemplates any form of the main arch passage 34', including slotted configurations. The auxiliary passage 40 is oriented in parallel-spaced relation (toward the gingival) to the main arch passage 34', the shank portion being bendable for anchoring to the second tooth bracket.

The retraction spring 20 also includes a loop portion 44 that extends between the stem portion 22 and the shank portion 36 for biasingly connecting the tooth brackets 28 and 42. Preferably the loop portion 44 is spaced from the stem portion 22 by a distance K for facilitating the coupling of desired torque components together with retraction forces. Accordingly, the spring 20 includes a leg segment 46, one end of the leg segment 46 being joined by a first curved segment 48 to the stem portion 22, the opposite end of the leg segment 46 being joined by a second curved segment 50 to the loop portion 44 as described below, the segments 48 and 50 being oppositely curved, forming with the leg segment 46 a Z-shaped leg portion 52 of the spring 20.

The loop portion 44, forming a T-shaped side profile outline, includes an upper segment 54, a pair of semicircular segments 56 joining respective opposite ends of the upper segment 54, a pair of arm segments 58 joining respective ones of the semicircular segments 56 opposite the upper segment 54, the arm segments 58 being aligned approximately parallel to the upper segment 54. A pair of upper quarter-circular segments 60 are joined to respective ones of the arm segments 58 opposite the corresponding semicircular segments 56, a pair of parallel-spaced column segments, designated first column segment 62a and second column segment 62b, joining respective ones of the upper quarter-circular segments 60 opposite the corresponding arm segments 58, the stem segments 62 being oriented approximately perpendicular to the upper segment 54. A lower quarter-circular segment 64 joins the second stem segment 62b opposite the corresponding upper quarter-circular segment 60 to the shank portion 36 such that the upper segment 54 and the arm segments 58 are oriented proximately in parallel coplanar relation with the shank portion 36. Thus the loop portion 44 is capable of transmitting a retractive tensile force from the shank portion 36 by tension and/or shear loading in combination with bending loading of the various loop segments 54, 56, 58, 60, 62, and 64. The retractive tensile force is further transmitted from the loop portion 44 to the stem portion 22 by means of the leg portion 52.

Figure 3:
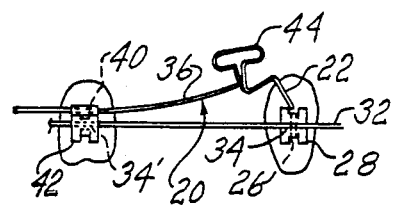
FIG. 3 is a side elevational view showing the spring of FIG. 1 being installed in a retraction system on a patient.

The curved segments 48, 50, 60, and 64 are formed with an inside radius R that can be a "minimum bend radius" such as 0.02 inch. The semicircular segments 56 are formed with a somewhat larger inside radius $R_2$, approximately 0.04 inch. The loop portion 44 extends lengthwise by a loop length E over the semicircular segments 56, the length E being approximately 0.29 inch, the loop portion 44 also having a loop height H above the shank portion 36, the height H being approximately 0.18 inch, the arm segments 58 being spaced below the top of the top segment 54 by a distance G of approximately 0.06 inch. The column segments 62 are relatively closely spaced, being confined within a column distance F that is typically approximately 0.06 inch. The shank portion 36 has a shank length L from the second column segment 62b, the length L being long enough to protrude the auxiliary passage 40 as shown in FIG. 3 when the brackets 28 and 42 are widely spaced, the protruding portion of the shank portion 36 being bent for locking to the second tooth bracket 42 as further described below. In most applications of the spring 20, the shank length L can be approximately 1.2 inches or less. The stem portion 22 has a stem length S (inclusive of the first curved segment 48), the length S being sufficient for protruding the vertical slot 26 and being similarly bent for locking to the first tooth bracket 28. Accordingly, the stem length S can be approximately 0.25 inch.

Figure 1:
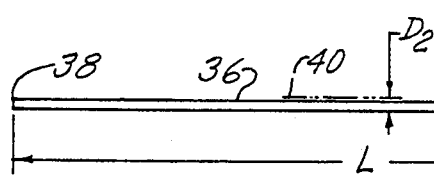
FIG. 1 is a side elevational view of an orthodontic retraction spring according to the present invention.

For the purpose of coupling a restoring moment to the first tooth bracket 28, the leg segment 46 is inclined upwardly by an angle A of approximately 30 degrees from the first leg segment 62a to the stem portion 22 relative to the shank portion 36, and the stem portion 22 forms an included angle B with the leg segment, the angle B being slightly greater than 90 degrees as shown in FIG. 1. Further, the first stem segment 62a is longer than the second stem segment 62b, the second curved segment extending below the shank portion 36 by a distance J for vertically aligning the first curved segment 48 approximately with the shank portion 36. Preferably the distance J is slightly greater than that required for such alignment, for providing clearance between the shank portion 36 and intervening brackets etc., if present.

Figure 6:
FIG. 6 is a fragmentary plan view of an alternative configuration of the spring of FIG. 1.
Figure 2:
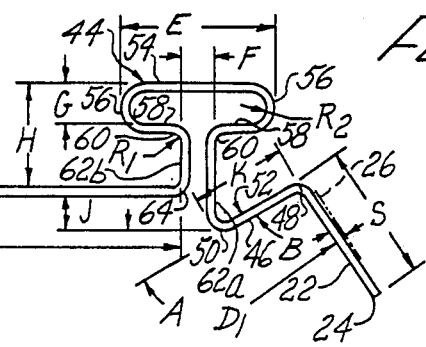
FIG. 2 is a front elevational view of the spring of FIG. 1.

With further reference to FIG. 6, the spring 20, which would normally be preformed in a coplanar configuration as shown in FIGS. 1 and 2, is further formed for transmitting a moment in compensation of tooth rotation. In particular, the leg segment 46 is angled out of the plane of the shank and loop portions 36 and 44 by an angle C about the first column segment 62a, the angle C being shown as positive for the inward projection of the stem portion 22 when the spring 20 is used in the right-side upper position. Moments in compensation of tooth rotation are transmitted from the stem portion 22 to the first tooth bracket 28 by means of non-circular engagement between the stem portion 22 and the vertically oriented slot 26.

As further shown in FIGS. 1, 2, and 6, the stem portion 22 fits within a slot depth $D_1$ and a slot width $W_1$ of the vertical slot 26 of the first tooth bracket 28. Similarly, the shank portion 36 fits within a passage depth $D_2$ and a passage width $W_2$ of the second tooth bracket 42. Preferably the spring 20 is formed with at least one of the depth d and the thickness t being a close slip fit within the respective depth D and width W of the corresponding tooth brackets 28 and 42 for limiting torsional backlash between the cross-sectional shape of the spring 20 and the respective brackets 28 and 42. Suitable brackets for use as the first tooth brackets 28 are available as 390-6 Series Mini Master bracket with vertical slot from American Orthodontics of Sheboygan, Wisc.. Such brackets have the depth $D_1$ formed at approximately 0.020 inch, the width $W_1$ also being approximately 0.020 inch. Similarly, brackets suitable for use as the second tooth brackets 42 are available as 004-9 Series first molar bracket with auxiliary tube, also from American Orthodontics, the depth $D_2$ and the width $W_2$ also being approximately 0.020 inch.

According to the present invention, the spring 20 has a relatively low tensile modulus or spring constant of less than approximately 50 grams per millimeter and being capable of coupling a bending moment to the first tooth bracket 28 when the shank portion 36 is tensioned as described herein, the bending moment being greater than approximately 500 gram-millimeters. This is achieved in the exemplary configuration of the spring 20 described herein by forming the spring 20 from a high-strength, low modulus spring alloy having rectangular cross-section. In particular, the spring 20 can be formed from beta-titanium, a nickel-titanium alloy, or an alloy of cobalt, the depth d and the thickness t each being approximately 0.017 inch. Alternatively, the spring 20 can be formed of corrosion-resistant steel, the depth d and the thickness t each being approximately 0.016 inch.

Figure 5:
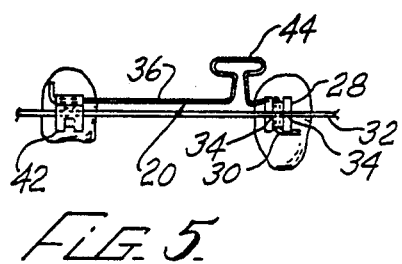
FIG. 5 is a side elevational view as in FIG. 3, showing completed installation.
Figure 4:
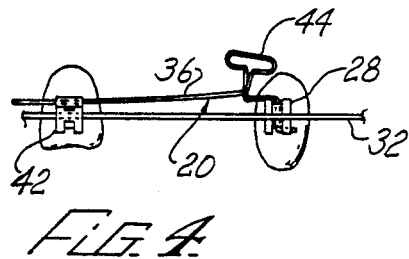
FIG. 4 is a side elevational view as in FIG. 3, showing a further stage of the installation.

According to the present invention, a method for retracting a patient's teeth includes the steps of: providing the first and second tooth brackets 28 and 42 anchored to respective teeth of the patient for engaging the continuous arch member 32, the first bracket 28 having the vertically oriented auxiliary slot 26, the second bracket 42 having the horizontally oriented auxiliary passage 34'; providing the retraction spring 20 including the high-strength elongate member having the stem portion 22, the shank portion 36, and the loop portion 44; feeding the shank portion 36 through the auxiliary passage 34' as shown in FIG. 3; feeding the stem portion 22 from the gingival through the vertical slot 26 (from the position shown in FIG. 3) while applying sufficient moment for vertically aligning the stem portion 22; bending a protruding portion 66 of the stem portion 22 for locking the stem portion 22 to the first bracket 28 as shown in FIG. 4; and bending a protruding portion 68 of the shank portion 36 while holding the portion 36 in an extending, tensioned condition as shown in FIG. 5, the spring 20 transmitting a relatively large restoring moment along with tension forces for avoiding undesired tipping of the retracting teeth.

Although the present invention has been described in considerable detail with reference to certain preferred versions thereof, other versions are possible. For example, The loop portion 44 can have other configurations such as an inverted U-shape, helical loop portions, and non-circularly curved segments. Also, other materials can be used in the spring 20. Therefore, the spirit and scope of the appended claims should not necessarily be limited to the description of the preferred versions contained herein.

What is claimed is:

1. An orthodontic retraction spring comprising a high-strength elongate member of uniform cross-section, the elongate member having:

(a) a stem portion at a first end of the spring for engaging a vertically oriented slot in a first tooth bracket, the stem portion being bendable for anchoring to the first tooth bracket;

(b) a shank portion extending from a second end of the spring for engaging an auxiliary passage in a second tooth bracket, the auxiliary passage being horizontally oriented in parallel-spaced relation to a main arch passage of the second tooth bracket, the shank portion being bendable for anchoring to the second tooth bracket; and (c) a loop portion connected between the stem portion and the shank portion for biasingly connecting the tooth brackets, the spring having a tensile spring constant of less than approximately 50 grams per millimeter and being capable of coupling a bending moment to the first tooth bracket, the bending moment being greater than approximately 500 gram-millimeters when the stem portion engages the vertically oriented slot in the first tooth bracket and the shank portion is anchored engaging the horizontally oriented auxiliary passage of the second tooth bracket.

2. The spring of claim 1, wherein the elongate member is of uniform rectangular cross-section.

3. The spring of claim 1, wherein the loop portion forms a T-shaped side profile outline having
   (a) an upper segment;
   (b) a pair of semicircular segments joining opposite ends of the upper segment;
   (c) a pair of arm segments joining respective ones of the semicircular segments opposite the upper segment, the arm segments being aligned approximately parallel to the upper segment;
   (d) a pair of upper quarter-circular segments joining respective ones of the arm segments opposite the corresponding semicircular segments;
   (e) first and second parallel-spaced column circular segments opposite the corresponding arm segments, the column segments being oriented approximately perpendicular to the upper segment; and
   (f) a lower quarter-circular segment joining the second stem segment opposite the corresponding upper quarter-circular segment, the lower quarter-circular segment joining the shank portion.

4. The spring of claim 1, wherein the elongate member is formed from a high strength alloy selected from the group consisting of a beta-titanium alloy, a nickel-titanium alloy, and an alloy of cobalt.

5. The spring of claim 4, wherein the uniform cross-section is square, having a thickness and depth of approximately 0.017 inch.

6. The spring of claim 1, wherein the elongate member is formed from a high strength corrosion resistant steel alloy.

7. The spring of claim 6, wherein the uniform cross-section is square, having a thickness and depth of approximately 0.016 inch.

8. An orthodontic retraction spring comprising a high-strength elongate member of uniform cross-section, the elongate member having:

(a) a stem portion at a first end of the spring for engaging a vertically oriented slot in a first tooth bracket, the stem portion being bendable for anchoring to the first tooth bracket;

(b) a shank portion extending from a second end of the spring for engaging an auxiliary passage in a second tooth bracket, the auxiliary passage being oriented in parallel-spaced relation to a main arch passage of the second tooth bracket, the shank portion being bendable for anchoring to the second tooth bracket;

(c) a loop portion forming a T-shaped side profile outline connected between the stem portion and the shank portion for biasingly connecting the tooth brackets, the spring having a tensile spring constant of less than approximately 50 grams per millimeter and being capable of coupling a bending moment to the first tooth bracket, the bending moment being greater than approximately 500 gram-millimeters; and (d) a Z-shaped leg portion connected between the loop portion and the stem portion, the leg portion having a leg segment, a first curved segment connecting a first end of the leg segment to the stem portion, and a second curved segment connecting the other end of the leg segment to the loop portion.

9. The spring of claim 8, wherein the leg segment is inclined upwardly by an angle A from the second curved segment to the first curved segment relative to the shank portion, and the stem portion forms an included angle B with the leg segment, the angle B being greater than 90 degrees.

10. The spring of claim 8, wherein the elongate member is formed from a high strength alloy selected from the group consisting of a beta-titanium alloy, a nickel-titanium alloy, and an alloy of cobalt.

11. The spring of claim 10, wherein the uniform cross-section is square, having a thickness and depth of approximately 0.017 inch.

12. The spring of claim 8, wherein the elongate member is formed from a high strength corrosion resistant steel alloy.

13. The spring of claim 12, wherein the uniform cross-section is square, having a thickness and depth of approximately 0.016 square.

14. An orthodontic retraction apparatus comprising:
   (a) a plurality of tooth brackets for rigid connection to corresponding teeth of a patient, each of the brackets being formed for engaging a continuous arch wire, with a main arch slot and having associated means for anchoring an arch wire tie, the tooth brackets including:
      (i) a first tooth bracket having an auxiliary slot for receiving an elongate member, the auxiliary slot being oriented in perpendicular relation to the main arch slot; and
      (ii) a second tooth bracket having an auxiliary passage therethrough, the auxiliary passage being oriented in parallel-spaced relation to the main arch passage; and
   (b) a retraction spring comprising a high-strength elongate member including:
      (i) a stem portion at a first end of the spring for engaging the vertical slot, the stem portion being bendable for anchoring to the first tooth bracket;
      (ii) a shank portion extending from a second end of the spring for engaging the auxiliary passage, the shank portion being bendable for anchoring to the second tooth bracket; and
      (iii) a loop portion connected between the stem portion and the shank portion for biasingly connecting the tooth brackets, the spring having a tensile spring constant of less than approximately 50 grams per millimeter and being capable of coupling a bending moment to the first tooth bracket, the bending moment being greater than approximately 500 gram-millimeters when the stem portion engages the vertically oriented slot in the first tooth bracket and the shank portion is anchored to the second tooth bracket.

15. The spring of claim 14, further comprising a Z-shaped leg portion connected between the loop portion and the stem portion, the leg portion having a leg segment, a first curved segment connecting a first end of the leg segment to the stem portion, and a second curved segment connecting the other end of the leg segment to the loop portion.

16. The spring of claim 15, wherein the leg segment is inclined upwardly by an angle A from the second curved segment to the first curved segment relative to the shank portion, and the stem portion forms an included angle B with the leg segment, the angle B being greater than 90 degrees.

17. The spring of claim 14, wherein the elongate member is formed from a high strength alloy selected from the group consisting of a beta-titanium alloy, a nickel-titanium alloy, and an alloy of cobalt.

18. The spring of claim 17, wherein the uniform cross-section is square, having a thickness and depth of approximately 0.017 inch.

19. The spring of claim 18, wherein the elongate member is formed from a high strength corrosion resistant steel alloy.

20. The spring of claim 19, wherein the uniform cross-section is square, having a thickness and depth of approximately 0.016 square.

21. A method for retracting a patient's teeth comprising the steps of:
   (a) providing first and second tooth brackets anchored to respective teeth of the patient for engaging a continuous arch wire, the first bracket having a vertically oriented auxiliary slot, the second bracket having a horizontally oriented auxiliary passage;
   (b) providing a retraction spring comprising a high-strength elongate member of uniform non-circular cross-section, including:
      (i) a stem portion at a first end of the spring for engaging the vertical slot, the stem portion being bendable for anchoring to the first tooth bracket;
      (ii) a shank portion extending from a second end of the spring for engaging the auxiliary passage, the shank portion being bendable for anchoring to the second tooth bracket; and
      (iii) a loop portion connected between the stem portion and the shank portion for biasingly connecting the tooth brackets, the spring having a tensile spring constant of less than approximately 50 grams per millimeter and being capable of coupling a bending moment to the first tooth bracket, the bending moment being greater than approximately 500 gram-millimeters;
   (c) feeding the shank of the spring through the auxiliary passage;
   (d) feeding the stem from the gingival through the vertical slot while applying sufficient moment for aligning the stem vertically;
   (e) bending a protruding portion of the stem for locking the stem to the first bracket; and
   (f) bending a protruding portion of the shank while holding the shank in an extending, tensioned condition, the spring transmitting a relatively large restoring moment along with tension forces for avoiding undesired tipping of the retracting teeth.

22. The method of claim 21, wherein the spring includes a leg portion between the loop portion and the stem portion, the loop and shank portions being coplanar, the method comprising the further steps of:
   (a) prior to the feeding steps forming the leg portion at an angle to the plane of the loop and shank portions; and
   (b) transmitting moments in compensation of tooth rotation by means of non-circular engagement between the stem and the vertical slot.

* * * * *